(12) United States Patent
Böttcher et al.

(10) Patent No.: US 8,815,870 B2
(45) Date of Patent: Aug. 26, 2014

(54) 4-(2-(6-SUBSTITUTED-HEXYLIDENE) HYDRAZINYL)BENZONITRILE AND PREPARATION THEREOF

(71) Applicant: Forest Laboratories Holdings Ltd., Hamilton (BM)

(72) Inventors: Henning Böttcher, Darmstadt (DE); Timo Heinrich, Gross-Umstadt (DE)

(*) Notice: Subject to any disclaimer, the term of this patent is extended or adjusted under 35 U.S.C. 154(b) by 0 days.

(21) Appl. No.: 13/932,098

(22) Filed: Jul. 1, 2013

(65) Prior Publication Data

US 2014/0005395 A1   Jan. 2, 2014

Related U.S. Application Data

(60) Provisional application No. 61/665,975, filed on Jun. 29, 2012.

(51) Int. Cl.

| | |
|---|---|
| *A61K 31/496* | (2006.01) |
| *C07D 405/12* | (2006.01) |
| *C07C 253/30* | (2006.01) |
| *C07C 255/66* | (2006.01) |

(52) U.S. Cl.
USPC .................. 514/254.09; 544/373; 558/422

(58) Field of Classification Search
None
See application file for complete search history.

(56) References Cited

U.S. PATENT DOCUMENTS 5,532,241 A * 7/1996 Bottcher et al. .......... 514/254.09

* cited by examiner

*Primary Examiner* — Kristin Vajda

(57) ABSTRACT

The present teachings provide a compound of Formula (I-B):

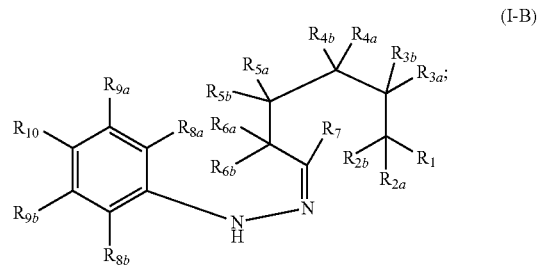

wherein $R_1$-$R_{10}$ are as described herein; a pharmaceutically acceptable salt of the compound, a geometric isomer of the compound, or a pharmaceutically acceptable salt of the geometric isomer. Also described are methods of preparing the same, as well as methods for preparing vilazodone using the same.

13 Claims, No Drawings

4-(2-(6-SUBSTITUTED-HEXYLIDENE) HYDRAZINYL)BENZONITRILE AND PREPARATION THEREOF

PRIORITY

This application claims priority from a corresponding U.S. provisional application 61/665,975 filed Jun. 29, 2012, which application is hereby incorporated by reference herein in its entirety.

BACKGROUND OF THE INVENTION

1-[4-(5-cyanoindol-3-yl)butyl]-4-(2-carbamoyl-benzofuran-5-yl)-piperazine, the hydrochloride salt of which is commonly known as vilazodone, is a dual selective serotonin reuptake inhibitor (SSRI)/5HT1A receptor partial agonist. Vilazodone can be used, for example, to treat major depressive disorders.

U.S. Pat. No. 5,532,241 discloses a method of preparing vilazodone. In this method, 3-(4-chlorobutyl)-5-cyanoindole is one of the key intermediates, which can be obtained by reaction of 5-cyanoindole with 4-chlorobutyryl chloride.

SUMMARY OF THE INVENTION

The present teachings are based, at least in part, on the discovery that novel substituted 1-hexylidene-2-phenylhydrazine compounds can be used as precursors of, e.g., 3-(4-chlorobutyl)-5-cyanoindole. Accordingly, these compounds, processes for preparing them, as well as processes for their use are disclosed herein. Without wishing to be bound by any particular theory, it is believed that compounds disclosed herein, for example the phenylhydrazine intermediates of formula (I-A) and (I-B), can provide advantages in the synthesis of indole-containing compounds such as vilazodone. Some advantages include, for example, higher conversion rates, greater product purity and the utilization of readily available hydrazine and aldehyde precursors.

One aspect of the present teachings relate to a compound of Formula (I-B):

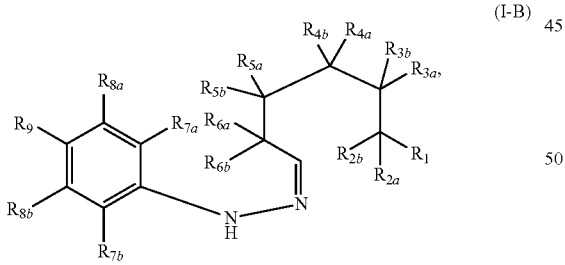

(I-B)

a pharmaceutically acceptable salt of the compound, a geometric isomer of the compound, or a pharmaceutically acceptable salt of the geometric isomer, wherein:

$R_1$ is a leaving group selected from halo, cyano, azido, —$OR^a$, —$OCOR^a$, —$OCOOR^a$, —$OCONR^aR^b$, —$NH_3^+$, —$NHR^aR^{b+}$, —$NR^aR^b$, —$OSO_2R^a$, and —$OP(O)(OR^a)_2$;

$R^a$ and $R^b$ are each independently selected from H, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ haloalkyl, optionally substituted 5 to 14 membered heteroaryl, and optionally substituted 6 to 14 membered aryl;

$R_{2a}$, $R_{2b}$, $R_{3a}$, $R_{3b}$, $R_{4a}$, $R_{4b}$, $R_{5a}$, $R_{5b}$, $R_{6a}$, and $R_{6b}$ are each independently selected from H, halo, $C_1$-$C_6$ alkyl, $C_1$-$C_6$ haloalkyl and —$OR^a$; and $R_{7a}$, $R_{7b}$, $R_{8a}$, $R_{8b}$, and $R_9$ are each independently selected from H, halo, cyano, $C_1$-$C_6$ alkyl, $C_1$-$C_6$ haloalkyl and —$OR^a$.

In some embodiments, leaving groups ($R_1$) include halo, cyano, azido, —$NH_3^+$, —$OSO_2F$, —$OSO_2CF_3$, —$OSO_2C_2F_5$, —$OSO_2PhCH_3$, —$OSO_2Ph$, and —$OSO_2CH_3$. In one embodiment, $R_1$ is selected from —I, —Br, and —Cl. In another embodiment, $R_1$ is —Cl.

In some embodiments, $R_{2a}$, $R_{2b}$, $R_{3a}$, $R_{3b}$, $R_{4a}$, $R_{4b}$, $R_{5a}$, $R_{5b}$, $R_{6a}$, and $R_{6b}$ are each independently selected from H, halo, —$CH_3$, —$CF_3$ and —$OCH_3$. For example, in one embodiment, $R_{2a}$, $R_{2b}$, $R_{3a}$, $R_{3b}$, $R_{4a}$, $R_{4b}$, $R_{5a}$, $R_{5b}$, $R_{6a}$, and $R_{6b}$ are each independently H.

In some embodiments, at least one $R_{7a}$, $R_{7b}$, $R_{8a}$, $R_{8b}$, and $R_9$ is cyano. In some embodiments, $R_{7a}$, $R_{7b}$, $R_{8a}$, $R_{9b}$, and $R_9$ are each independently selected from H, halo, cyano, —$CH_3$, —$CF_3$ and —$OCH_3$. In one embodiment, $R_{7a}$, $R_{7b}$, $R_{8a}$, $R_{8b}$, and $R_9$ are each independently H; and $R_9$ is cyano.

Exemplary compounds of Formula (I-B) are (Z)-4-(2-(6-iodohexylidene)hydrazinyl)benzonitrile, (Z)-4-(2-(6-bromohexylidene)hydrazinyl)benzonitrile, (Z)-4-(2-(6-chloro hexylidene)hydrazinyl)benzonitrile, (E)-4-(2-(6-iodohexylidene)hydrazinyl)benzonitrile, (E)-4-(2-(6-bromohexylidene)hydrazinyl)benzonitrile, (E)-4-(2-(6-chloro hexylidene)hydrazinyl)benzonitrile a pharmaceutically acceptable salt of the compound, a geometric isomer of the compound, or a pharmaceutically acceptable salt of the geometric isomer.

Another aspect of the present teachings relate to a process of preparing a compound of Formula (I-B):

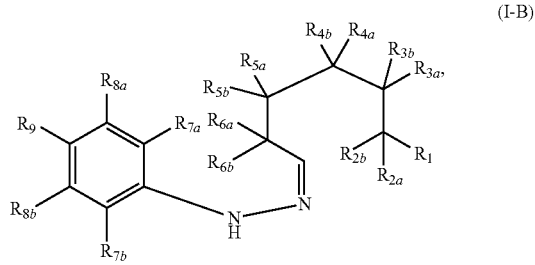

(I-B)

a pharmaceutically acceptable salt of the compound, a geometric isomer of the compound, or a pharmaceutically acceptable salt of the geometric isomer, wherein:

the process comprising reacting a compound of Formula (II)

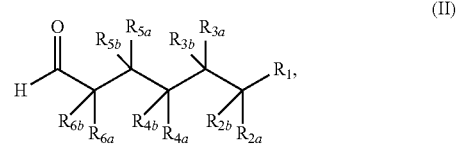

(II)

with a compound of Formula (III):

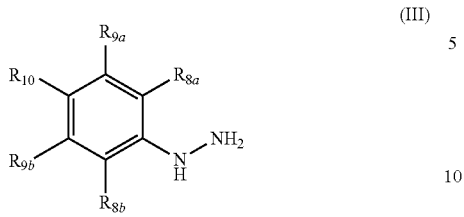

or a pharmaceutically acceptable salt thereof; wherein:

$R_1$ is a leaving group selected from halo, cyano, azido, —$OR^a$, —$OCOR^a$, —$OCOOR^a$, —$OCONR^aR^b$, —$NH_3^+$, —$NHR^aR^{b+}$, —$NR^aR^b$, —$OSO_2R^a$, and —$OP(O)(OR^a)_2$. In one embodiment, $R_1$ is —Cl.

$R^a$ and $R^b$ are each independently selected from H, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ haloalkyl, optionally substituted 5 to 14 membered heteroaryl, and optionally substituted 6 to 14 membered aryl;

$R_{2a}$, $R_{2b}$, $R_{3a}$, $R_{3b}$, $R_{4a}$, $R_{4b}$, $R_{5a}$, $R_{5b}$, $R_{6a}$, and $R_{6b}$ are each independently selected from H, halo, $C_1$-$C_6$ alkyl, $C_1$-$C_6$ haloalkyl and —$OR^a$; and $R_{7a}$, $R_{7b}$, $R_{8a}$, $R_{8b}$, $R_{9a}$, $R_{9b}$, $R_{10}$ are each independently selected from H, halo, cyano, $C_1$-$C_6$ alkyl, $C_1$-$C_6$ haloalkyl and —$OR^a$.

The process is optionally conducted in the presence of a base, such as trimethylamine, triethylamine, N,N-diisopropylethylamine, dimethylaniline, or pyridine.

Still another aspect of the present teachings relate to a process of preparing a compound of Formula (VI):

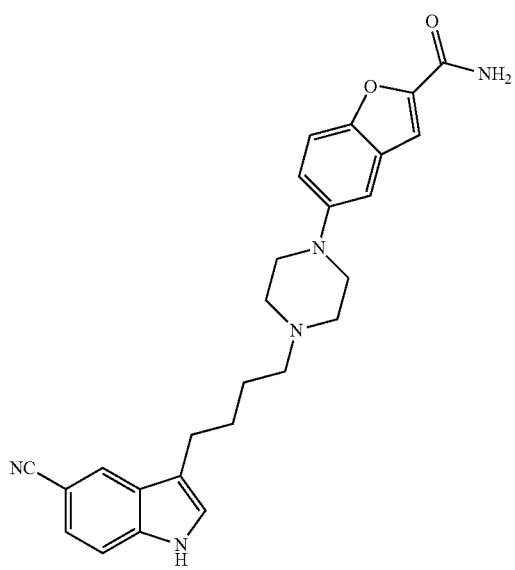

a pharmaceutically acceptable salt of the compound, an isomer of the compound, or a pharmaceutically acceptable salt of the isomer; the process comprising:

contacting a compound of Formula (I')

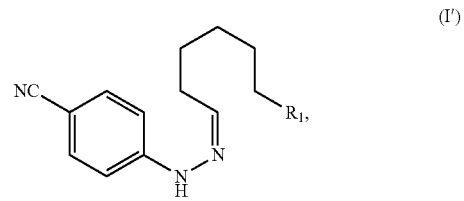

with an acid, to form a compound of Formula (IV)

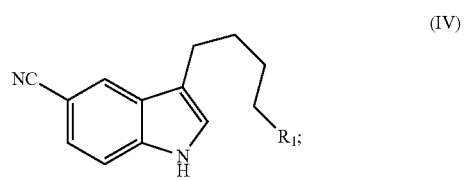

wherein:

$R_1$ is a leaving group selected from halo, cyano, azido, —$OR^a$, —$OCOR^a$, —$OCOOR^a$, —$OCONR^aR^b$, —$NH_3^+$, —$NHR^aR^{b+}$, —$NR^aR^b$, —$OSO_2R^a$, and —$OP(O)(OR^a)_2$; and $R^a$ and $R^b$ are each, independently, selected from H, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ haloalkyl, optionally substituted 5 to 14 membered heteroaryl, and optionally substituted 6 to 14 membered aryl. In one embodiment, $R_1$ is —Cl.

The process of preparing a compound of Formula (VI) can further comprise reacting the compound of Formula (IV) with a compound of Formula (V):

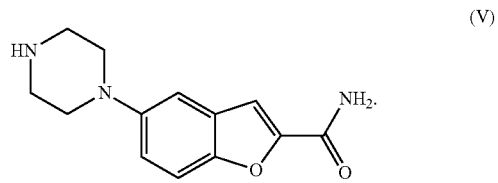 [SMILES: NC(=O)c1cc2cc(N3CCNCC3)ccc2o1]

Another aspect of the present teachings relate to a compound of Formula (VI) or a pharmaceutically acceptable salt thereof prepared by a process comprising:

contacting a compound of Formula (I')

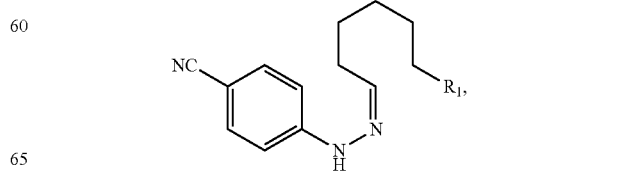

with an acid, to form a compound of Formula (IV)

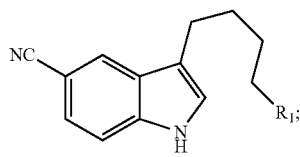

(IV)

reacting the compound of Formula (IV) with a compound of Formula (V)

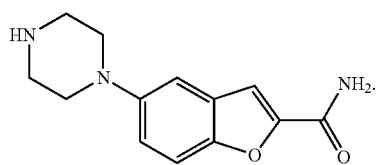

(V)

wherein:
R$_1$ is a leaving group selected from halo, cyano, azido, —OR$^a$, —OCOR$^a$, —OCOOR$^a$, —OCONR$^a$R$^b$, —NH$_3^+$, —NHR$^a$R$^{b+}$, —NR$^a$R$^b$, —OSO$_2$R$^a$, and —OP(O)(OR$^a$)$_2$; and R$^a$ and R$^b$ are each independently selected from H, optionally substituted C$_1$-C$_{10}$ alkyl, optionally substituted C$_2$-C$_{10}$ alkenyl, optionally substituted C$_2$-C$_{10}$ alkynyl, optionally substituted C$_1$-C$_{10}$ haloalkyl, optionally substituted 5 to 14 membered heteroaryl, and optionally substituted 6 to 14 membered aryl, thereby preparing the compound of Formula (VI) or a pharmaceutically acceptable salt thereof, wherein the compound of Formula (VI) is present together with the compound of Formula (I') at an amount less than 1.5 micrograms/day. In one embodiment, R$_1$ is Cl.

Another aspect of the present invention relates to the compound of Formula (VI) or a pharmaceutically acceptable salt thereof, wherein the compound of Formula (I') is present at an amount less than about 0.75 mg/kg. In one embodiment, the compound of Formula (I') is present at an amount not more than 37.5 mg/kg.

Yet another aspect of the present invention relate to the compound of Formula (VI) or a pharmaceutically acceptable salt thereof, wherein the compound of Formula (VI) has a purity of at least 90% as measured by HPLC. In one embodiment, the compound of Formula (VI) has a purity of at least 95% as measured by HPLC. In another embodiment, the compound of Formula (VI) has a purity of at least 99% as measured by HPLC.

The details of one or more embodiments of the present teachings are set forth in the description below. Other features, objects, and advantages of the present teachings will be apparent from the description of examples and also from the appending claims.

DETAILED DESCRIPTION OF THE INVENTION

The present teachings are directed, at least in part, to methods and compounds useful in the synthesis of compounds having activity on the central nervous system, e.g., antidepressant activity. In some embodiments, the compounds described herein have pharmacological properties, such as activity on the central nervous system.

Compounds

In some embodiments, the present teachings provide compounds of Formula (I.A):

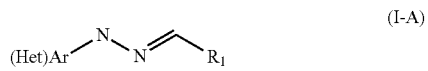

(I-A)

pharmaceutically acceptable salts of the compound, geometric isomers of the compound, and pharmaceutically acceptable salts of the geometric isomer; wherein R$_1$ is a leaving group; and (Het)Ar— is a group selected from optionally substituted 5 to 14 membered heteroaryl and optionally substituted 6 to 14 membered aryl.

In some embodiments, the present teachings provide compounds of Formula (I-B):

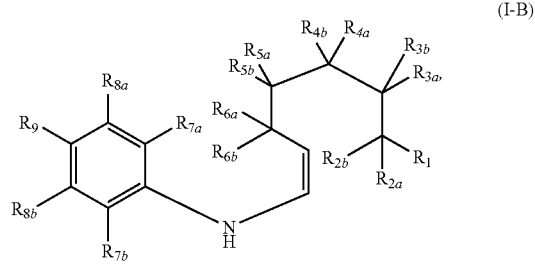

(I-B)

pharmaceutically acceptable salts of the compound, geometric isomers of the compound, and pharmaceutically acceptable salts of the geometric isomer; wherein R$_1$ is a leaving group;

R$_{2a}$, R$_{2b}$, R$_{3a}$, R$_{3b}$, R$_{4a}$, R$_{4b}$, R$_{5a}$, R$_{5b}$, R$_{6a}$, and R$_{6b}$ are each independently selected from H, halo, C$_1$-C$_6$ alkyl, C$_1$-C$_6$ haloalkyl and —OR$^a$; and R$_{7a}$, R$_{7b}$, R$_{8a}$, R$_{8b}$, and R$_9$ are each independently selected from H, halo, cyano, C$_1$-C$_6$ alkyl, C$_1$-C$_6$ haloalkyl and —OR$^a$.

As used herein, a "leaving group" refers to a moiety that departs the core molecule with a pair of electrons in heterolytic bond cleavage. Exemplary leaving groups are known to the skilled artisan. (See, e.g., Smith, M. B. et al., March's Advanced Organic Chemistry, Reactions, Mechanism, and Structure, 5$^{th}$ Ed., 2001). Leaving groups include, but are not limited to diazonium salts (—N$_2^+$), oxonium ions (—OR$_2^+$), halides (e.g., —Cl, —Br, —I), sulfonate esters and fluorinated sulfonate esters (e.g., tosylate, mesylate, —OSO$_2$C$_4$F$_9$, —OSO$_2$CF$_3$, —OSO$_2$F), ammonium salts (—NR$_3^+$), alcohols and ethers, as well as their conjugate acids (—OH, —OH$_2^+$, —OR, —OHR$^+$), nitrates, phosphates, thioethers (—SR$_2^+$), cyano, azido, carboxylic acids, esters, and acid anhydrides.

In one embodiment, R$_1$ is selected from halo, cyano, azido, —OR$^a$, —OCOR$^a$, —OCOOR$^a$, —OCONR$^a$R$^b$, —NH$_3^+$, —NHR$^a$R$^{b+}$, —NR$^a$R$^b$, —OSO$_2$R$^a$, and —OP(O)(OR$^a$)$_2$; and R$^a$ and R$^b$ are each, independently, selected from H, optionally substituted C$_1$-C$_{10}$ alkyl, optionally substituted C$_2$-C$_{10}$ alkenyl, optionally substituted C$_2$-C$_{10}$ alkynyl, optionally substituted C$_1$-C$_{10}$ haloalkyl, optionally substituted 5 to 14 membered heteroaryl, and optionally substituted 6 to 14 membered aryl. In some embodiments, R$^a$ and R$^b$ are each independently selected from H, C$_1$-C$_{10}$ alkyl, C$_2$-C$_{10}$ alkenyl, C$_2$-C$_{10}$ alkynyl, C$_1$-C$_{10}$ haloalkyl, 5 to 14 membered heteroaryl, and 6 to 14 membered aryl. In some embodiments, R$^a$ and R$^b$ are each independently selected from H, C$_1$-C$_6$ alkyl, C$_2$-C$_6$ alkenyl, C$_2$-C$_6$ alkynyl, C$_1$-C$_6$ haloalkyl, and phenyl.

In one embodiment, $R_1$ is selected from halo, cyano, azido, —$OR^a$, —$OCOR^a$, —$OCOOR^a$, —$OCONR^aR^b$, —$OSO_2R^a$, and —$OP(O)(OR^a)_2$; and $R^a$ and $R^b$ are each, independently, selected from H, optionally substituted $C_1$-$C_{10}$ alkyl, optionally substituted $C_2$-$C_{10}$ alkenyl, optionally substituted $C_1$-$C_{10}$ haloalkyl, optionally substituted 5 to 14 membered heteroaryl, and optionally substituted 6 to 14 membered aryl.

As noted above, leaving group denotes a group which leaves during the reaction. In some embodiments, leaving groups include halo, cyano, azido, —$NH_3^+$, —$OSO_2F$, —$OSO_2CF_3$, —$OSO_2C_2F_5$, —$OSO_2PhCH_3$, —$OSO_2Ph$, and —$OSO_2CH_3$. In one embodiment, $R_1$ is selected from I, Br, and Cl. In one embodiment, $R_1$ is Cl.

In some embodiments, $R_{2a}$, $R_{2b}$, $R_{3a}$, $R_{4b}$, $R_{5a}$, $R_{5b}$, $R_{6a}$, and $R_{6b}$ are each independently selected from H, halo, —$CH_3$, —$CF_3$ and —$OCH_3$. In certain embodiments, $R_{2a}$, $R_{2b}$, $R_{3a}$, $R_{3b}$, $R_{4a}$, $R_{4b}$, $R_{5a}$, $R_{5b}$, $R_{6a}$, and $R_{6b}$ are each independently selected from H, halo, and —$CH_3$. In other embodiments, each of $R_{2a}$, $R_{2b}$, $R_{3a}$, $R_{3b}$, $R_{4a}$, $R_{4b}$, $R_{5a}$, $R_{5b}$, $R_{6a}$, and $R_{6b}$ is H.

In some embodiments, at least one $R_{7a}$, $R_{7b}$, $R_{8a}$, $R_{8b}$, and $R_9$ is cyano. In some embodiments, $R_9$ is cyano. In some embodiments, $R_{7a}$, $R_{7b}$, $R_{8a}$, $R_{8b}$, and $R_9$ are each independently selected from H, halo, cyano, —$CH_3$, —$CF_3$ and —$OCH_3$. In certain embodiments, $R_{7a}$, $R_{7b}$, $R_{8a}$ and $R_{8b}$ are each independently selected from H, halo, and —$CH_3$; and $R_9$ is cyano. In certain embodiments, each of $R_{7a}$, $R_{7b}$, $R_{8a}$ and $R_{8b}$ are H; and $R_9$ is cyano.

In some embodiments, $R_{2a}$, $R_{2b}$, $R_{3a}$, $R_{3b}$, $R_{4a}$, $R_{4b}$, $R_{5a}$, $R_{5b}$, $R_{6a}$, and $R_{6b}$ are each independently selected from H, halo and —$CH_3$; and $R_{7a}$, $R_{7b}$, $R_{8a}$, $R_{8b}$, and $R_9$ are each independently selected from H, halo, cyano and —$CH_3$. In other embodiments, each of $R_{2a}$, $R_{2b}$, $R_{3a}$, $R_{3b}$, $R_{4a}$, $R_{4b}$, $R_{5a}$, $R_{5b}$, $R_{6a}$, and $R_{6b}$ is H; each of $R_{7a}$, $R_{7b}$, $R_{8a}$ and $R_{8b}$ are H; and $R_9$ is cyano. In such embodiments, $R_1$ is as generically, subgenerically and specifically defined above.

In some embodiments, $R_1$ is halo; $R_{2a}$, $R_{2b}$, $R_{3a}$, $R_{3b}$, $R_{4a}$, $R_{4b}$, $R_{5a}$, $R_{5b}$, $R_{6a}$, $R_{6b}$ are each independently selected from H, halo and —$CH_3$; and $R_{7a}$, $R_{7b}$, $R_{8a}$, $R_{8b}$, and $R_9$ are each independently selected from H, halo, cyano and —$CH_3$. In other embodiments, $R_1$ is halo (e.g., —Cl); each of $R_{2a}$, $R_{2b}$, $R_{3a}$, $R_{3b}$, $R_{4a}$, $R_{4b}$, $R_{5a}$, $R_{5b}$, $R_{6a}$, and $R_{6b}$ is H; each of $R_{7a}$, $R_{7b}$, $R_{8a}$ and $R_{8b}$ is H; and $R_9$ is cyano.

Exemplary compounds of Formula (I-B) are (Z)-4-(2-(6-iodohexylidene)hydrazinyl)benzonitrile, (Z)-4-(2-(6-bromohexylidene)hydrazinyl)benzonitrile, (Z)-4-(2-(6-chlorohexylidene)hydrazinyl)benzonitrile, a pharmaceutically acceptable salt of the compound, a geometric isomer of the compound, or a pharmaceutically acceptable salt of the geometric isomer.

In certain embodiments, the present teachings provide the compounds depicted and/or described by name herein, as well as neutral forms and pharmaceutically acceptable salts thereof.

Unless otherwise specified, the below terms used herein are defined as follows:

The term "alkyl" used alone or as part of a larger moiety, such as "haloalkyl", and the like, means saturated aliphatic straight-chain or branched monovalent hydrocarbon radical. Unless otherwise specified, an alkyl group typically has 1-10 carbon atoms, i.e., ($C_1$-$C_{10}$)alkyl. As used herein, a "($C_1$-$C_{10}$) alkyl" group means a radical having from 1 to 10 carbon atoms in a linear or branched arrangement.

The term "alkenyl" means branched or straight-chain monovalent hydrocarbon containing at least one double bond. Alkenyl may be mono or polyunsaturated hydrocarbon, and may exist in the E or Z configuration. Unless otherwise specified, an alkenyl group typically has a minimum of 2 carbon atoms, i.e., ($C_2$)alkenyl.

"Alkynyl" means branched or straight-chain monovalent hydrocarbon containing at least one triple bond. Unless otherwise specified, an alkynyl group typically has a minimum 2 of 2 carbon atoms, i.e., ($C_2$)alkynyl.

"Alkoxy" means an alkyl radical attached through an oxygen linking atom, represented by —O-alkyl. For example, "($C_1$-$C_4$)alkoxy" includes methoxy, ethoxy, propoxy, and butoxy.

The terms "haloalkyl" and "haloalkoxy" means alkyl or alkoxy, as the case may be, substituted with one or more halogen atoms. The term "halo" or "halogen" means F, Cl, Br, or I. Preferably the halogen in haloalkyl is F.

The term "aryl" means an aromatic hydrocarbon ring system. The term "aryl" may be used interchangeably with the terms "aryl ring" "aromatic ring", "aryl group" and "aromatic group". An aryl group typically has six to fourteen ring atoms. Examples includes phenyl, naphthyl, anthracenyl, 1,2-dihydronaphthyl, 1,2,3,4-tetrahydronaphthyl, fluorenyl, indanyl, indanyl and the like. A "substituted aryl group" is substituted at any one or more substitutable ring atom, which is a ring carbon atom bonded to a hydrogen.

The term "heteroaryl", "heteroaromatic", "heteroaryl ring", "heteroaryl group", "heteroaromatic ring", and "heteroaromatic group", are used interchangeably herein. "Heteroaryl" refers to aromatic ring groups having five to fourteen ring atoms selected from carbon and at least one (typically 1 to 4, more typically 1 or 2) heteroatoms (e.g., oxygen, nitrogen, or sulfur). "Heteroaryl" includes monocyclic rings and polycyclic rings in which a monocyclic heteroaromatic ring is fused to one or more other aromatic or heteroaromatic rings. As such, "5-14 membered heteroaryl" includes monocyclic, bicyclic, or tricyclic ring systems.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl). Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen.

Unless otherwise indicated, suitable substituents for an alkyl, alkenyl, alkynyl, haloalkyl, aryl group, and heteroaryl group include those substituents which form a stable compound of the invention without significantly adversely affecting the reactivity of the compound of the invention. Examples of substituents for alkyl, alkenyl, alkynyl, haloalkyl, aryl, and heteroaryl include optionally substituted alkyl, optionally substituted alkenyl, optionally substituted alkynyl, optionally substituted aryl, optionally substituted heteroaryl, optionally substituted haloalkyl, optionally substituted heteroalkyl, optionally substituted alkoxy, optionally substituted haloalkoxy, halo, cyano, azido, —$OR^a$, —$OCOR^a$, —OCOOR$^a$, —OCONR$^a$R$^b$, —NH$_3^+$, —NR$^a$R$^b$, —OSO$_2$R$^a$, and —OP(O)(OR$^a$)$_2$.

Regarding connectivity, a "haloalkyl" moiety, for example, refers to an alkyl group substituted with a halo group (e.g., pentafluoroethyl, —C$_2$F$_5$). Similarly, a "haloalkoxy" moiety refers to an alkoxy group substituted with a halo group.

The present teachings also include various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geometric isomers in the mixture.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g., (+)-tartrates, (−)-tartrates or mixtures thereof including racemic mixtures], succinates, benzoates and salts with amino acids such as glutamic acid.

Methods

In some embodiments, the present teachings provide processes for preparing a compound of Formula (I-B):

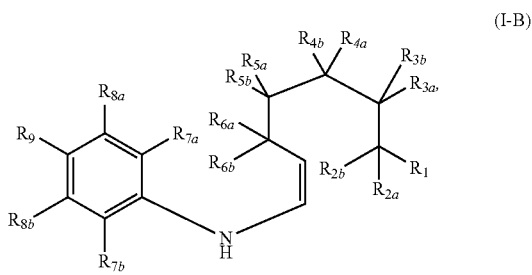

a pharmaceutically acceptable salt of the compound, a geometric isomer of the compound, or a pharmaceutically acceptable salt of the geometric isomer, wherein R$_1$ is a leaving group. The process generally includes reacting a compound of Formula (II):

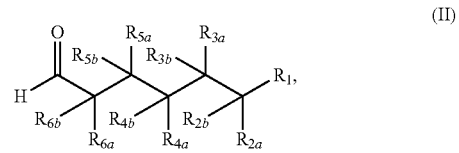

with a compound of Formula (III):

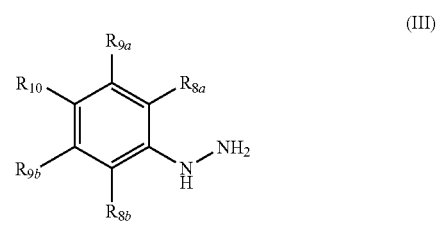

or a pharmaceutically acceptable salt thereof. Suitable groups for R$_1$, R$_{2a}$, R$_{2b}$, R$_{3a}$, R$_{3b}$, R$_{4a}$, R$_{4b}$, R$_{5a}$, R$_{5b}$, R$_{6a}$, R$_{6b}$, R$_{7a}$, R$_{7b}$, R$_{8a}$, R$_{8b}$, R$_{9a}$, R$_{9b}$ and R$_{10}$ are enumerated hereinabove (generically, subgenerically and specifically) in connection with compounds of Formula (I-B).

In some embodiments, the process is conducted in the presence of a base. The base can be, for example, an organic base or an inorganic base. Organic bases include, but are not limited to, secondary or tertiary amines. Such bases include, for example, trimethylamine, triethylamine, N,N-diisopropylethylamine, dimethylaniline, and pyridine. Inorganic bases include, but are not limited to, potassium carbonate, sodium carbonate, lithium carbonate and hydrogen carbonate. In some embodiments, the process is conducted in the presence of triethylamine. In some embodiments, the base is introduced at a reduced temperature (e.g., a temperature below ambient room temperature).

In some embodiments, the pK$_b$ of the compound of Formula (III) is such that little or no base is needed in the reaction. For example, it is noted that when free base 4-cyanophenylhydrazine is used, the process can proceed with catalytic amounts of base, or even with no base.

The process is typically conducted in the presence of a suitable solvent. In some embodiments, the solvent is a hydrocarbon solvent. In some embodiments, the solvent is a high boiling point ether. Suitable solvents include, but are not limited to, hexanes, toluene, benzene, chlorobenzene, xylene, n-hexane, heptane, cyclohexane, methylcyclohexane, tetrahydrofuran, 1,4-dioxane and mixtures thereof.

In some embodiments, the reaction mixture is warmed and maintained at a temperature between about 20° C. and about 70° C., e.g., between 20° C. and 50° C. In some embodiments, the reaction mixture is warmed and maintained at a temperature above about room temperature.

In some embodiments, compounds described herein can be prepared using the reaction scheme and syntheses described below, employing techniques available in the art using starting materials that are readily available.

Scheme 1

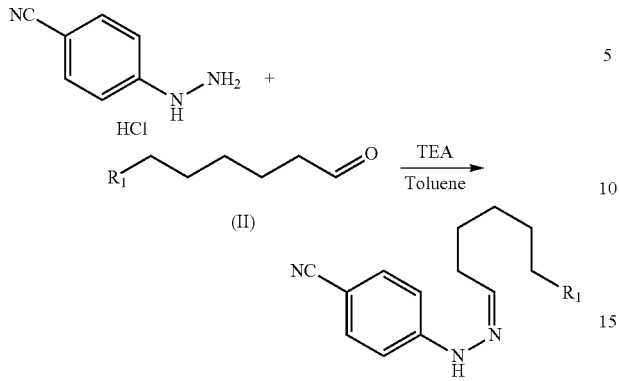

As shown in Scheme 1, in an exemplary process according to the present teachings, 6-substituted hexanol and commercially available 4-cyanophenylhydrazine HCl are dissolved or suspended in a solvent. To this mixture is added a suitable base, such as trimethylamine, triethylamine, N,N-diisopropylethylamine, dimethylaniline, and/or pyridine. The resultant mixture is warmed to a temperature at about room temperature or above until the reaction is complete. The target compound formed in this way is obtained by conventional work-up.

The compounds of Formula II can be readily prepared by oxidation of corresponding primary alcohol to aldehyde, which is widely known in the art. (See Smith, M. B. et al., March's Advanced Organic Chemistry, Reactions, Mechanism, and Structure, 5$^{th}$ Ed., 2001). For example, when $R_1$ is —$OR^a$, —$OCOR^a$, —$OCOOR^a$, —$OCONR^aR^b$, —$OSO_2R^a$, and —$OP(O)(OR^a)_2$, they can be converted from a primary alcohol by etherification, esterification, and acylation.

The substances prepared with the aid of the processes described above can serve as precursors for the synthesis of antidepressants, such as vilazodone. Accordingly, in some embodiments, the present teachings provide a process for preparing a compound of Formula (VI):

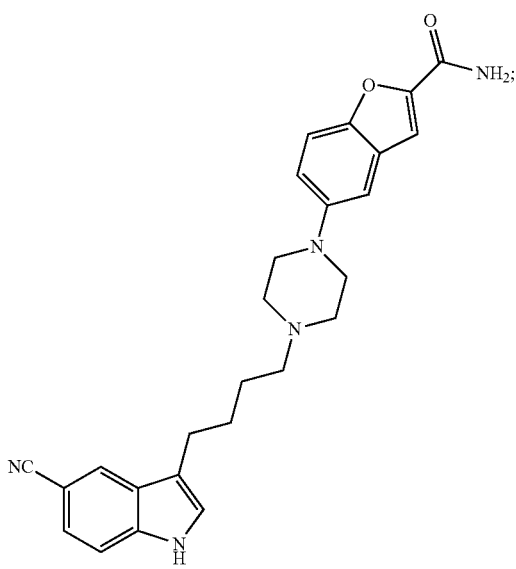

a pharmaceutically acceptable salt of the compound, an isomer of the compound, or a pharmaceutically acceptable salt of the isomer.

The process generally includes contacting a compound of Formula (I')

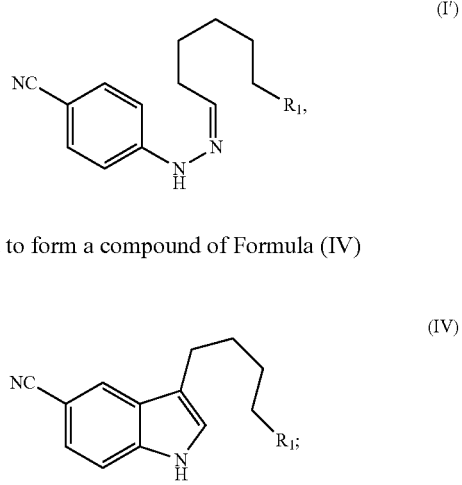

with an acid to form a compound of Formula (IV)

(IV)

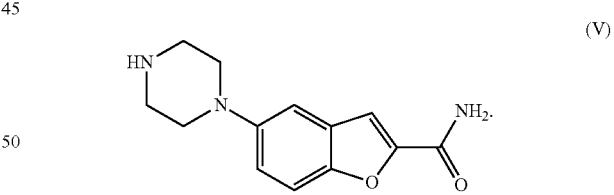

wherein $R_1$ is a leaving group. In one embodiment, $R_1$ is —Cl. In some embodiments, the compound of Formula (I') is reacted with an acid in a suitable solvent.

In some embodiments, the acid is a strong acid, such as a strong inorganic acid. Strong acids include, but are not limited to, hydrochloric acid, nitric acid, sulfuric acid, phosphoric acid, perchloric acid, hydrobromic acid, fluorosulfonic acid, chlorosulfonic acid, trifluoroacetic acid, methanesulfonic acid, benzenesulfonic acid, p-toluenesulfonic acid, and trifluoromethanesulfonic acid. For example, in some embodiments, the acid is phosphoric acid, e.g., 85% phosphoric acid. In some embodiments, contacting a compound of Formula (I') with an acid occurs in the presence of a suitable solvent. In some embodiments, contacting a compound of Formula (I') with an acid does not require any solvent.

In some embodiments, the method further includes reacting the compound of Formula (IV) with a compound of Formula (V)

(V)

Suitable leaving groups ($R_1$) are described hereinabove. In some embodiments, $R_1$ is selected from halo, cyano, azido, —$OR^a$, $OCOR^a$, —$OCOOR^a$, —$OCONR^aR^b$, —$NH_3^+$, —$NHR^aR^{b+}$, —$NR^aR^b$, —$OSO_2R^a$, and —$OP(O)(OR^a)_2$; and $R^a$ and $R^b$ are each independently selected from H, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ haloalkyl, optionally substituted 5 to 14 membered heteroaryl, and optionally substituted 6 to 14 membered aryl. In some embodiments, $R_1$ is selected from halo, cyano, azido, $OR^a$, —$OCOR^a$, —$OCOOR^a$, —$OCONR^aR^b$, —$OSO_2R^a$, and —$OP(O)(OR^a)_2$; and $R^a$ and $R^b$ are each independently selected from H, optionally substituted $C_1$-$C_{10}$ alkyl, optionally substituted $C_2$-$C_{10}$ alkenyl, optionally substituted $C_1$-$C_{10}$ haloalkyl, optionally substituted 5 to 14 membered heteroaryl, and optionally substituted 6 to 14 membered aryl. In some embodiments, $R^a$ and $R^b$ are each, independently, selected from H, $C_1$-$C_{10}$ alkyl, 5 to 14 membered heteroaryl, and 6 to 14 membered aryl.

The compound of Formula (IV) is typically reacted with a compound of Formula (V) in the presence of a solvent and, in some embodiments, in the presence of a suitable base. A suitable solvent includes, but is not limited to, N-methyl-2-pyrrolidone, N,N-dimethylformamide, acetonitrile, acetone, dimethylsulfoxide, N,N-dimethylacetamide, 1,4-dioxane, pyridine, tetrahydrofuran and mixtures thereof. Suitable bases include, but are not limited to organic and inorganic bases. Organic bases include, but are not limited to, secondary or tertiary amines, such as trimethylamine, triethylamine, N,N-diisopropylethylamine dimethylaniline, or pyridine. Inorganic bases include, but are not limited to, potassium carbonate, sodium carbonate, lithium carbonate and hydrogen carbonate.

In some embodiments, the steps in the process of forming a compound of Formula (VI) are carried out at specific temperatures, e.g., elevated temperatures. For example, in some embodiments, the reaction of the compound of Formula I with an acid is carried out at a temperature of between about 30° C. and about 100° C. In some embodiments, the reaction of the compound of Formula III with the compound of Formula IV is carried out at a temperature of between about 30° C. and about 150° C.

In some embodiments, the present teachings provide a compound of Formula (VI) or a composition comprising a compound of Formula (VI), which is prepared by a process described herein. In some embodiments, the present teachings provide a compound of Formula (VI) or a composition comprising a compound of Formula (VI), which is prepared utilizing one or more intermediates described herein. Such a compound/composition may have advantages over those formulated in the art, for example in terms of purity, yield, stability and/or presence of (or absence of) specific polymorphic forms.

One skilled in the art would be aware of different chromatographic methods that are contemplated to be used for demonstrating purity of the compound of Formula (VI) or a pharmaceutical salt thereof. In one embodiment, the compound of Formula (VI) or a salt thereof is at least 90% pure as measured by High Performance Liquid Chromatography (HPLC). In another embodiment, the compound of Formula (VI) or a salt thereof is at least 95% pure as measured by HPLC. In yet another embodiment, the compound of Formula (VI) or a salt thereof is at least 99% pure as measured by HPLC.

Several impurities may be found together with the compound of Formula (VI), or in a pharmaceutically acceptable salt of the compound of Formula (VI). For example, the presence of a compound of Formula (I-B), or a pharmaceutically acceptable salt of the compound of Formula (I-B) that may be found with a compound of Formula (VI) may be tightly controlled and restricted in order to comply with acceptable levels for potential impurities present in the final pharmaceutical product. For example, a dose of 1.5 micrograms/day has been described as the acceptable level for impurities in pharmaceuticals. (See, e.g., FDA Draft Guidance, Genotoxic and Carcinogenic Impurities in Drug Substances and Products: Recommended Approaches, December 2008).

The highest possible maximum dose for a compound of Formula (I-B), or a pharmaceutically acceptable salt of the compound of Formula (I-B) is about 1.5 µg/active ingredient daily dose. In this regard, the compound of Formula (I-B), a pharmaceutically acceptable salt of the compound may be controlled to less than about 1.5 micrograms/day or 37.5 mg/kg in a compound of Formula (VI) or in a pharmaceutically acceptable salt of the compound of Formula (VI).

In some embodiments, the compound of Formula (I-B), or a pharmaceutically acceptable salt of the compound is controlled to less than about 0.75 mg/kg in a compound of Formula (VI) or in a pharmaceutically acceptable salt of the compound of Formula (VI). In some other embodiments, the compound of Formula (I-B), a pharmaceutically acceptable salt of the compound is controlled to less than about 0.5 mg/kg in a compound of Formula (VI) or in a pharmaceutically acceptable salt of the compound of Formula (VI). In yet another embodiment, the compound of Formula (I-B), a pharmaceutically acceptable salt of the compound is controlled to less than about 0.3 mg/kg in a compound of Formula (VI) or in a pharmaceutically acceptable salt of the compound of Formula (VI).

EXAMPLES

Example 1

Synthesis of 6-Chlorohexanal

6-Chlorohexanol (18 g) and toluene (about 0.1 L) are charged to a suitable vessel. The mixture is cooled to 0° C., and 2,2,6,6-tetra-methylpiperidine-1-oxyl (TEMPO, about 0.01 equiv.) and sodium bicarbonate (about 0.9 equiv.) are added. The mixture is stirred and 5% sodium hypochlorite aqueous solution (NaOCl aq., about 1.05 equiv.) is added. The reaction mixture is maintained below 0° C. until the reaction is complete. The organic layer is separated and washed sequentially with 10% sodium thiosulfate aqueous solution, water, and saturated sodium chloride aqueous solution to give a 6-chlorohexanal/toluene solution, which is used directly in the next step.

Example 2

Synthesis of (Z)-4-(2-(6-chlorohexylidene)hydrazinyl)benzonitrile

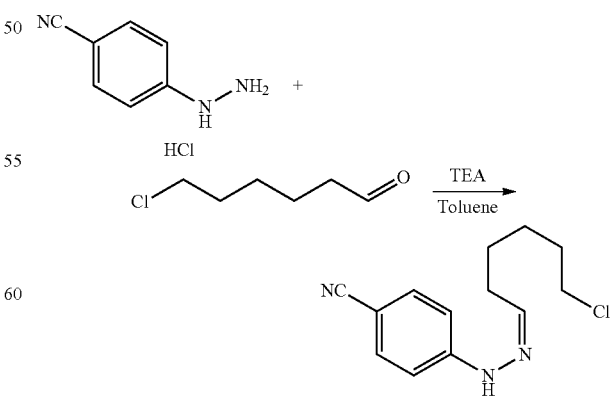

To a mixture of 4-cyanophenylhydrazine HCl (3.44 g, 20.3 mM) and 6-chlorohexanal (2.5 g, 18.6 mM) in toluene (30 mL) was added triethylamine at 0° C. (2.82 mL, 20.3 mM). The mixture was allowed to stir for 2 hours at ambient temperature. The mixture was filtered and the resultant filter cake was washed with toluene. The combined filtrate was concentrated under vacuum to give 4.92 g of a crude product, which was purified using conventional methods to yield 4.16 g (89.6%) of 4-(2-(6-chlorohexylidene)hydrazinyl)benzonitrile as a mixture of cis:trans isomers (ratio 5:1). NMR (400 MHZ, CDCl$_3$): 7.6-6.6 (6H, (4H, dd-aromatic; 1H (m)-N$\underline{H}$, 1H (t)-N=C$\underline{H}$-t)), 3.57 (2H (t), C$\underline{H}_2$Cl), 2.2-2.4 (2H (m), =CH—C$\underline{H}_2$), 1.75-1.90 (2H (m), CH$_2$Cl—C$\underline{H}_2$), 1.49-1.65 (4H (m), C$\underline{H}_2$—C$\underline{H}_2$); m/z: 250 [M+H]+, calcd for [C$_{13}$H$_{16}$ClN$_3$+H]$^+$ 250.10.

Example 3

Synthesis of 3-(4-chlorobutyl)-1H-indole-5-carbonitrile

85% Phosphoric acid (about 7.8 equiv.) is charged to the 4-(2-(6-chlorohexylidene)hydrazinyl)benzonitrile solution of Example 2, and the reaction mixture is heated to 65° C. to 75° C. until the reaction is complete. Conventional washing and workup leads to the crude product. Purification is carried out via conventional means known in the art, e.g., washing, filtration and precipitation.

Example 4

Synthesis of Vilazodone 3-(4-chlorobutyl)-1H-indole-5-carbonitrile (1.01 g, 1.0 equiv.), 5-(piperazin-1-yl)benzofuran-2-carboxamide (1.10 g, 1.03 equiv.), diisopropylethyl amine (DIPEA, 0.64 g, 1.16 equiv.), and N-Methyl-2-pyrrolidone (NMP, about 40 mL) are charged to a suitable vessel. It is to be noted that 5-(piperazin-1-yl)benzofuran-2-carboxamide may be produced using methods known in the art (see, e.g., U.S. Pat. No. 5,977,112). The mixture is heated and stirred until the reaction is complete. Acetonitrile (about 40 mL) and water (about 40 mL) are charged while maintaining elevated temperature. The mixture is cooled slowly to precipitate vilazodone, filtered, and the wet cake is washed with acetonitrile/water and then with acetonitrile. The wet product is dried to provide crude vilazodone. Purification is carried out via conventional means known in the art, e.g., filtration and precipitation.

It is to be noted that vilazodone HCl can be produced from vilazodone using methods known in the art.

EQUIVALENTS

While this invention has been particularly shown and described with references to example embodiments thereof, it will be understood by those skilled in the art that various changes in form and details may be made therein without departing from the scope of the invention encompassed by the appended claims

What is claimed is:

1. A process for preparing a compound of Formula (VI):

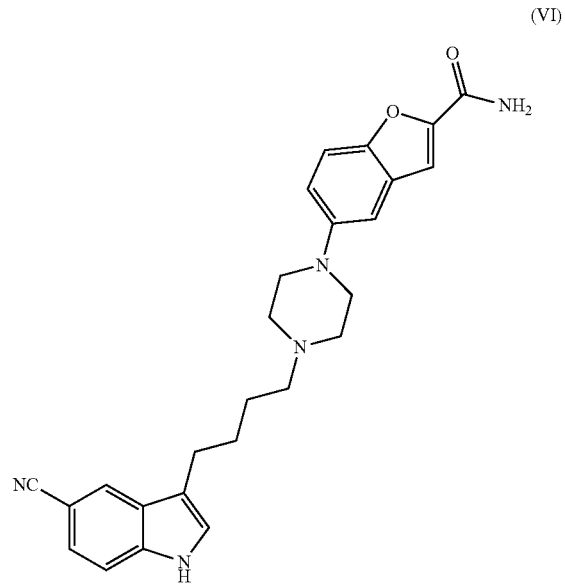 [SMILES: N#Cc1ccc2[nH]cc(CCCCN3CCN(c4ccc5oc(C(N)=O)cc5c4)CC3)c2c1]

(VI)

a pharmaceutically acceptable salt of the compound, an isomer of the compound, or a pharmaceutically acceptable salt of the isomer;

the process comprising:

contacting a compound of Formula (I')

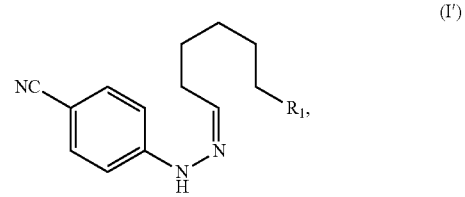

(I')

with an acid, to form a compound of Formula (IV)

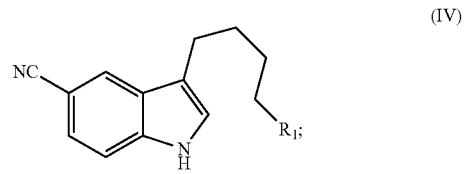

(IV)

wherein:

R$_1$ is a leaving group selected from halo, cyano, azido, —OR$^a$, —OCOR$^a$, —OCOOR$^a$, —OCONR$^a$R$^b$, —NH$_3^+$, —NHR$^a$R$^{b+}$, —NR$^a$R$^b$, —OSO$_2$R$^a$, and —OP(O)(OR$^a$)$_2$; and R$^a$ and R$^b$ are each independently selected from H, optionally substituted C$_1$-C$_{10}$ alkyl, optionally substituted C$_2$-C$_{10}$ alkenyl, optionally substituted C$_2$-C$_{10}$ alkynyl, optionally substituted C$_1$-C$_{10}$ haloalkyl, optionally substituted 5 to 14 membered heteroaryl, and optionally substituted 6 to 14 membered aryl.

2. The process of claim 1, further comprising:
reacting the compound of Formula (IV) with a compound of Formula (V)

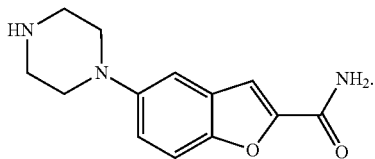
(V)

3. The process of claim 1, wherein $R_1$ is selected from halo, cyano, azido, —OSO$_2$F, —OSO$_2$CF$_3$, —OSO$_2$C$_2$F$_5$, —OSO$_2$PhCH$_3$, —OSO$_2$Ph, and —OSO$_2$CH$_3$.

4. The process of claim 3, wherein $R_1$ is selected from I, Br, and Cl.

5. A compound of Formula (VI) or a pharmaceutically acceptable salt thereof prepared by a process comprising:
contacting a compound of Formula (I')

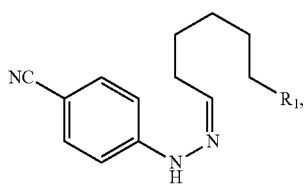
(I')

with an acid, to form a compound of Formula (IV)

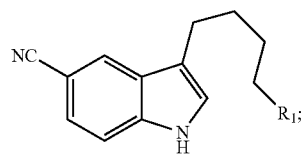
(IV)

reacting the compound of Formula (IV) with a compound of Formula (V)

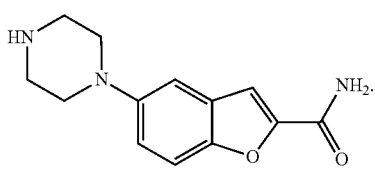
(V)

wherein:

$R_1$ is a leaving group selected from halo, cyano, azido, —OR$^a$, —OCOR$^a$, —OCOOR$^a$, —OCONR$^a$R$^b$, —NH$_3^+$, —NHR$^a$R$^{b+}$, —NR$^a$R$^b$, —OSO$_2$R$^a$, and —OP(O)(OR$^a$)$_2$; and R$^a$ and R$^b$ are each independently selected from H, optionally substituted C$_1$-C$_{10}$ alkyl, optionally substituted C$_2$-C$_{10}$ alkenyl, optionally substituted C$_2$-C$_{10}$ alkynyl, optionally substituted C$_1$-C$_{10}$ haloalkyl, optionally substituted 5 to 14 membered heteroaryl, and optionally substituted 6 to 14 membered aryl, thereby preparing the compound of Formula (VI) or a pharmaceutically acceptable salt thereof, wherein the compound of Formula (I') is present together with the compound of Formula (VI) at an amount greater than zero and less than 1.5 micrograms/day relative to maximum daily dose/day of the compound of Formula (VI).

6. The compound of claim 5, wherein $R_1$ is Cl.

7. The compound of claim 5, wherein the compound of Formula (I') is present at an amount greater than zero and less than about 0.75 mg/kg relative to the compound of Formula (VI).

8. The compound of claim 5, wherein the compound of Formula (I') is at an amount greater than zero and not more than 37.5 mg/kg relative to maximum daily dose/day of the compound of Formula (VI).

9. The compound of claim 5, wherein the compound of Formula (VI) has a purity of at least 90% as measured by HPLC.

10. The compound of claim 5, wherein the compound of Formula (VI) has a purity of at least 95% as measured by HPLC.

11. The compound of claim 5, wherein the compound of Formula (VI) has a purity of at least 99% as measured by HPLC.

12. A pharmaceutical composition comprising the compound of Formula (I') and the compound of Formula (VI) according to claim 5.

13. The pharmaceutical composition of claim 12 comprising up to 1.5 micrograms/day of the compound of Formula (I') or a pharmaceutically acceptable salt thereof, relative to maximum daily dose/day of the compound of Formula (VI).

* * * * *